(12) United States Patent
Crescenzi et al.

(10) Patent No.: US 7,585,460 B2
(45) Date of Patent: Sep. 8, 2009

(54) METHOD FOR INHIBITING THE BIOLOGICAL ACIDIFICATION OF WATER IN CONTACT WITH MATERIALS CONTAINING SULFUR

(75) Inventors: Francesco Crescenzi, Rome (IT); Antonella Crisari, Rome (IT); Cesare Achille Piatti, Milan (IT)

(73) Assignees: ENI S.p.A., Rome (IT); Enitecnologie S.p.A., San Donato Milanese (IT)

( * ) Notice: Subject to any disclaimer, the term of this patent is extended or adjusted under 35 U.S.C. 154(b) by 688 days.

(21) Appl. No.: 10/831,139

(22) Filed: Apr. 26, 2004

(65) Prior Publication Data

US 2005/0002825 A1    Jan. 6, 2005

(30) Foreign Application Priority Data

Apr. 30, 2003    (IT) .......................... MI2003A0882

(51) Int. Cl.
```
C23F 11/04     (2006.01)
C23F 11/00     (2006.01)
C23F 11/16     (2006.01)
A61L 9/00      (2006.01)
E21C 37/00     (2006.01)
B01D 24/00     (2006.01)
C02F 1/42      (2006.01)
C02F 1/72      (2006.01)
C02F 1/68      (2006.01)
A01N 59/26     (2006.01)
A01N 37/00     (2006.01)
E21B 33/13     (2006.01)
```

(52) U.S. Cl. ................ 422/1; 422/12; 422/14; 422/15; 422/28; 422/29; 422/900; 422/37; 422/3; 422/18; 422/32; 210/749; 210/759; 210/763; 210/764; 210/285; 210/688; 424/613; 424/614; 424/615; 424/616; 424/618; 424/619; 424/601; 424/604; 424/19; 424/22; 514/363; 514/392; 514/557; 514/558; 514/559; 514/560; 514/495; 514/970; 166/292; 299/11

(58) Field of Classification Search .............. 422/1, 422/12, 14–15, 900, 28–29, 37, 3, 18, 32; 210/749, 759, 763–764, 285, 688; 424/613–616, 424/618–619, 601, 604, 19, 22, 30; 514/363, 514/392, 557–560, 495, 970; 166/292; 299/11
See application file for complete search history.

(56) References Cited

U.S. PATENT DOCUMENTS

| | | | | | |
|---|---|---|---|---|---|
| 3,388,058 | A | * | 6/1968 | Wirth, Jr. ............. | 210/673 |
| 3,443,882 | A | * | 5/1969 | Flynn ..................... | 422/3 |
| 3,847,788 | A | * | 11/1974 | Wallace ................. | 204/633 |
| 4,314,966 | A | * | 2/1982 | Kleinmann ............ | 422/28 |
| 4,637,759 | A | * | 1/1987 | Owa et al. ............. | 405/270 |
| 5,550,141 | A | * | 8/1996 | Gould et al. .......... | 514/363 |
| 6,277,414 | B1 | * | 8/2001 | Elhaik et al. ......... | 424/616 |
| 6,419,836 | B1 | * | 7/2002 | Willuweit .............. | 210/749 |
| 6,582,025 | B2 | * | 6/2003 | Pickren ................. | 299/6 |
| 6,651,383 | B2 | * | 11/2003 | Grott .................... | 47/58.1 SC |

OTHER PUBLICATIONS

Internet Printout for definition of Molar Concentration from empria.edu website.*
Interntet Printout for definition of Normal from unc.edu website.*

* cited by examiner

*Primary Examiner*—Jill Warden
*Assistant Examiner*—Monzer R. Chorbaji
(74) *Attorney, Agent, or Firm*—Oblon, Spivak, McClelland, Maier & Neustadt, P.C.

(57) ABSTRACT

The invention relates to a method for inhibiting the biological acidification of water which is in contact with materials containing sulfur in reduced form or with elemental sulfur, susceptible to oxidation on the part of *Thiobacilli*, comprising putting said materials in contact with soluble inorganic salts at concentrations ranging from 0.4 normal to saturation.

8 Claims, No Drawings

METHOD FOR INHIBITING THE BIOLOGICAL ACIDIFICATION OF WATER IN CONTACT WITH MATERIALS CONTAINING SULFUR

The present invention relates to a method for inhibiting the biological acidification of water which comes into contact with materials containing sulfur.

More specifically, the invention relates to a method for inhibiting the acidification of water which comes into contact with materials containing sulfur in reduced form or with elemental sulfur, susceptible to oxidation on the part of *Thiobacilli*.

Sulfur is a material which is non-toxic but which creates significant environmental risks when large quantities are moved or deposited.

Due to the current depression in the world market of elemental sulfur, it is predicted, for example, that a consistent part of the sulfur recovered from the desulfuration of fossil fuels will have to be deposited for a long period of time. This sulfur is a compulsory production and will tend to increase in the near future together with the production of energy; forecasts, in fact, estimate an expected surplus of sulfur in 2010 equal to 5-7 million t/y, but it may turn out to be much higher.

For the above reasons, industries which treat elemental sulfur must become capable of handling, in an environmentally correct way, the problem deposit the material for more or less long periods of time and this may become a key point for the sulfur industry and for oil companies which exploit hydrocarbon reserves containing high concentrations of sulfur.

The lack of environmentally acceptable solutions, on the other hand, could even endanger the oil production of acid reservoirs.

Although the depositing of even large quantities of sulfur has been widely put into practice (Canada has been handling millions of tons of sulfur deposits for various decades), attention has only recently been paid to the environmental aspects associated with these deposits.

When facing this problem, the current drop in the price of this element, which has further restricted the economic margins available for an environmentally correct handling of sulfur, should be taken into consideration.

The greatest environmental risks in sulfur deposits derive from the formation of extremely acidic percolates which arise from the contact between rain water and the surface of the sulfur.

Acidic percolates can pollute the soil and groundwater, and can also increase the solubility of heavy metals present in the soil, transferring them into the groundwater.

The acidification of water which comes into contact with elemental sulfur is the result of the oxidation of the element on the part of the micro-organism *Thiobacillus*, capable of the following reaction:

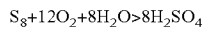

$$S_8 + 12O_2 + 8H_2O > 8H_2SO_4$$

The micro-organism takes the carbon which it needs from the atmosphere as $CO_2$ (it is autotrophous) and only requires small quantities of other elements (N, P, micronutrients) practically always present in all unrestricted environments, for surviving.

*Thiobacillus* is omnipresent and has a fundamental role in the natural biological cycle of sulfur. Among other things, the ubiquity of *Thiobacillus* allows the use of elemental sulfur for satisfying the sulfur requirement of agricultural crops.

*Thiobacilli* have been the object of detailed research studies over the years and have demonstrated their capacity of also surviving in acidic environments or in the presence of concentrated inorganic salts.

With respect to the inhibition of acidification of the water produced by *Thiobacilli*, studies carried out in the past were mainly oriented towards reducing the risk of corrosion of metallic structures in contact with sulfur.

These studies led to the identification of bacteriostatic products such as Sodium Lauryl Sulfate, which has proved to be effective for reducing the corrosion of metallic containers used for transporting or containing sulfur. (Clark P. D., Hyne J. B, Laishley E. J. and Bryant R. D., Result of ship Trials on the use of SLS for inhibition of acid build-up in elemental sulfur, Proc. Sulphur '98, British Sulphur Publishing, Nov. 1-4, 1998, Tucson Ariz., pages 29-43).

The use of bacteriostatic products for solving the problem of acidification in unrestricted environments, as in the case of acid percolates from sulfur deposits, cannot however be proposed.

Repeated applications of biocides are in fact necessary in order to ensure inhibition over a prolonged period of time and this creates a considerable increase in costs and risks for the environment due to the large quantities of biocide which must be adopted.

With the exception of deposits in closed environments of small quantities of elemental sulfur, the only industrial solution currently adopted on a wide scale for the storage of elemental sulfur consists in forming large blocks of the material in open-air spaces. (Clark P. D., Sulphur Storage and utilization for power generation ASRL Review., Sulphur, October 2001 Nr. 276, pages 39-42).

The rainwater which comes into contact with the sulfur block is collected and sent to treatment plants before entering surface waterworks.

This solution, however, is rather expensive as it necessitates the collection and total treatment of rill and infiltration water and in any case has significant risks for the environment.

An approximate estimate published recently (Clark P. D.: Sulphur storage and utilization for power generation ASRL Review, Sulphur, October 2001 Nr. 276 pages 39-42) calculates that the treatment of rill water coming from sulfur deposits situated in the Canadian region of Alberta can reach a cost of as much as 3 $ per ton of sulfur per year.

For deposits containing millions of tons of sulfur, the running cost can consequently reach values in the order of millions of dollars a year.

It is known from literature that some species of *Thiobacilli*, with the exception of halophilic strains, are sensitive to the presence in the culture medium of mineral salts. (Suzuki I., Lee D: Mackay B. Effect of various ions, pH and osmotic pressure on oxidation of elemental sulfur by *Thiobacillus thiooxidans*, Applied and Environmental Microbiology, November 1999, pages 5163-5168; Harahuc L., Lizama H. and Suzuki I., Selective inhibition of the oxidation of ferrous iron or sulfur in *Thiobacillus ferrooxidans*, Applied and Environmental Microbiology, March 2000, pages 1031-1037.

A simple and economical method has now been found, which is based on the use of solutions of inorganic salts and which inhibits the acidification, produced by *Thiobacilli*, of water which comes in contact with materials containing sulfur in reduced form or with elemental sulfur.

The method has proved to be effective regardless of the type of *Thiobacilli* possibly present on the surface of the sulfur.

In accordance with this, an object of the present invention relates to a method for inhibiting the biological acidification of water which comes into contact with materials containing sulfur in reduced form or with elemental sulfur, susceptible to oxidation on the part of *Thiobacilli*, comprising putting said materials in contact with soluble inorganic salts at concentrations ranging from 0.4 normal to saturation.

The inorganic salts at the concentrations of the invention, exert a bacteriostatic action on the *Thiobacilli*, thus preventing a lowering of the pH, which remains close to neutrality.

The possibility of inhibiting the acidification of water in contact with materials containing sulfur using the bacteriostatic action of suitably concentrated saline solutions has not as yet been described in literature.

If the saline concentration, however, is brought by dilution to lower levels than those necessary for the inhibition, the acidification is normally re-established. In order to obtain the desired effect, it is therefore necessary to maintain the concentration of the solution in contact with the *Thiobacilli* at the established levels.

The method of the invention can be usefully applied not only in the handling of sulfur deposits but also in the handling of all sulfur-based materials such as, for example, some minerals or metallic sulfides.

By operating according to the method of the invention, it is possible to handle deposits of elemental sulfur for long periods of time, in an environmentally correct way and at much lower costs than those to be sustained with the methods currently available.

In order to obtain the necessary effect to inhibit acidification, inorganic salts can be used, which are harmless from an environmental point of view, such as chlorides, sulfates, nitrates of mono- or bivalent cations with concentrations ranging from 0.4 Normal to saturation.

NaCl is preferably used, at a concentration ranging from 0.5 equivalents/liter and saturation.

Various methods can be used in the handling of sulfur deposits, for maintaining the effective concentration of salt on the surface of the sulfur.

For example, when it is possible to predict the submersion of sulfur in water, as in the case of sulfur deposits positioned below groundwater level or in waterproofed lagoons, the inhibition effect can be simply obtained by producing and maintaining the necessary concentration of salt in the submersion water.

For non-submersed storage systems, it is necessary, on the contrary, to prevent the salt from being washed away from the surface of the sulfur by protecting it with a suitable cover.

This can be effected with a waterproof material which is certainly effective for preventing the salt from being washed away, but has the disadvantage of being costly due to the wide extension of the sulfur deposits, and are also risky due to the possibility of the accumulation, over a period of time, of extremely dangerous toxic gases between the cover and the sulfur.

Alternatively, a low cost cover can be produced with inert granulated materials of a suitable thickness optionally containing small quantities of hydraulic binders to prevent erosion. This cover is permeable to gases and effective for preventing the salt from being washed away.

For this purpose, the following materials have proved to be effective: sand, breccia, pozzolan, and as binders, lime or cement. Alternatively, soil or excavation materials can be used.

After saturating the layer of the cover with rainwater, the impermeability of the sulfur surface prevents the formation of a vertical flow which would wash away the salt, whereas the horizontal flow of the water which reaches the surface of the sulfur can be easily prevented with containment walls having a height less than or equal to the thickness of the coating.

In relation to the amount of rain expected in the specific site destined for storing the sulfur, a thickness of the cover is selected which is such as to minimize diffusion phenomena of the salt towards the surface of the coating layer.

In the case of a decrease in the concentration of the salt to values lower than necessary, this will be re-established with suitable additions of concentrated saline solutions.

Numerous systems capable of guaranteeing a complete inhibition of water acidification, can be used for applying the salt to the surface of the sulfur.

The easiest system consists in spreading the inorganic salt in powder form on the surface of the sulfur before applying the coating, in other cases it may be more convenient to spray the surface of the sulfur with concentrated saline solutions.

Another application system which has proved to be effective even if slightly more complex, consists in englobing the salt in the sulfur mass, by finely dispersing it in liquid sulfur at concentrations ranging from 5 to 20% by weight and spreading the suspension on the surface of the sulfur mass in storage.

In this way the salt becomes part of the structure, it protects the sulfur from acidification and is in turn partially protected from washing phenomena.

A further application system consists in inserting the sulfur below the groundwater level, when this is sufficiently saline.

This happens quite commonly in countries of the world where saline groundwater is present very close to the surface.

The storage of sulfur below the groundwater level would, in these cases, not only inhibit acidification, but also hide the deposits from sight.

EXAMPLES

Operating Procedure of Acidification Tests of Water in Contact with Elemental Sulfur Bacterial organisms of the *Thiobacillus* type are described in literature as being mainly responsible for the oxidation, in natural environments, of elemental sulfur up to sulfuric acid and consequently acidification of water in contact with elemental sulfur.

Microbial strains belonging to the above species were therefore used for the setting up of experimental tests oriented towards the protection and mitigation of acido-genesis.

The tests were carried out using microbial strains purchased from public collections and bacterial isolates selected from materials removed from sulfur deposits, and also in volcanically active areas known for the presence of sulfur and emission of sulfides.

Example 1

Preparation of Trigger Cultures of *Thiobacilli* a) Cultivation of Strains Purchased from Public Collections.

Strains of *Thiobacillus thiooxidans* DSM 504, *T. thioparus* DSM 505, *T. ferrooxidans* DSM 583, purchased in lyophilized form, were revivified on the media and under the conditions indicated by the collection supplier DSMZ.

The grown cells were used for the sowing of liquid cultures of each strain in the specific media (25 ml in 100 ml flasks).

For the preparation of a culture of inoculum consisting of collection micro-organisms, 25 ml aliquots of the saline TM medium formulated as follows, were introduced into 100 ml wide-necked flasks: $K_2HPO_4$ (3.5 g/l), $(NH_4)_2SO_4$ (0.3 g/l) $MgSO_4$ $7H_2O$ (0.5 g/l) $FeSO_4$ $7H_2O$ (0.018 g/l), $CaCl_2$ (0.25 g/l) (Starkey 1935, Waksman and Joffe 1922). The phosphates were sterilized separated and then joined to the other components of the medium (sterilized in an autoclave with vapour for 20 minutes at 121° C.).

The TM medium was regulated to pH 6 with a solution of HCl 0.1 N, and 0.1 g (0.4%) of elemental sulfur (sulfur powder 98%-UNI sieved: 0.05) were added.

The culture medium was inoculated with 0.5 ml of a mixed bacterial suspension—containing $10^8$ cells/ml—obtained from the mixture of pure cultures of *Thiobacillus thiooxidans, T. thioparus, T. ferrooxidans* previously prepared.

The cultures were incubated under bland orbital stirring (100 rpm) for 25 days. At the end of this period, the culture broths were filtered on common filter paper—to eliminate the excess sulfur—to be preserved, in 2 ml aliquots, in polypropylene phials, in a refrigerator at −70° C.

b) Cultivation of Sulfo-Oxidizing Strains of the Wild Type Selected in Laboratory 25 ml of TM medium (regulated to pH 6 with HCl 0.1 N and sterilized in an autoclave with vapour for 20 minutes at 121° C.) were introduced into 100 ml flasks. 0.1 g (0.4%) of elemental sulfur (sulfur powder 98%-UNI sieved:0.05) were added to the TM culture medium. 2 g of small sulfur fragments taken from a sulfur deposit in Canada exposed for years to the outside environment and consequently definitely contaminated by sulfo-oxidizing bacteria, were added to the medium as a source of micro-organisms. The cultures were incubated under bland orbital stirring (100 rpm) for 25 days. During the incubation, the cultures were controlled daily for the indirect quantitative evaluation of the cellular development by registering the optical density value (at 600 nm) and to measure the lowering of the pH value.

At the end of this period, the culture broths obtained, with a cellular density higher than $10^7$ cells/ml and a lowering of the pH of the medium to a value of 1.5, were filtered on common filter paper to eliminate the particles of excess sulfur and to be preserved, in 2 ml aliquots, in polypropylene phials, in a refrigerator at −70° C., as standardized inoculum.

The two consortia: that produced starting from collection strains and the one prepared starting from sulfur samples removed from actual deposits, were compared with respect to the growth curves and acidification capacity. The comparison revealed practically identical growth kinetics and acidification. It was then decided to use, for the whole following experiment, the trigger culture consisting of the wild type strains selected from the natural environment. This culture is hereafter called "consortium".

Example 2

Verification of the Microbial Colonization of Surfaces of Elemental Sulfur

Preparation of the Colonization Tests 200 ml of culture broths of *Thiobacilli* in TM medium at pH 6 and 2 sulfur tablets (about 13 g each prepared by solidification of liquid sulfur in aluminum moulds), were introduced into borosilicate glass containers (open beakers, diameter=14 cm, H=7 cm). The containers were incubated for 25 days at room temperature, covered at the top with blotting paper to guarantee the passage of air and prevent pollution of the test-samples.

This procedure allowed an effective colonization of the exposed surfaces of the sulfur test-samples on the part of *Thiobacilli*.

The acidification of the solution in contact with the sulfur deriving from the oxidation was verified by registering the variations in pH in the liquid medium.

The colonization of the surface of the sulfur test-samples with bacterial cells was observed with a scanning electronic microscope (SEM).

Example 3

Inhibition Effect of NaCl on the Acidification of Water in Contact with Sulfur Powder Inoculated with a Culture of *Thiobacilli*

25 ml of TM—in demineralized water—at pH 6, inoculated with 0.4% (vol/vol) of the bacterial suspension (consortium), with the addition of 0.1 g of sulfur powder, were introduced into 100 ml flasks. 33 g/l of NaCl were added to the medium to evaluate the inhibiting effect of the salt on the growth of the *Thiobacilli* and the acidification of the solution. Control cultures without NaCl were incubated parallelly.

The culture broths were controlled for pH and absorbance variations.

The results obtained are indicated in Table 1.

TABLE 1

| Time | pH | | Optical density | |
|---|---|---|---|---|
| (days) | +NaCl | −NaCl | −NaCl | +NaCl |
| 0 | 6.0 | 6.0 | 0.021 | 0.021 |
| 1 | 6.0 | 6.0 | 0.038 | 0.025 |
| 3 | 6.0 | 6.0 | 0.041 | 0.024 |
| 5 | 5.8 | 3.5 | 0.080 | 0.028 |
| 9 | 5.8 | 2.2 | 0.190 | 0.021 |
| 12 | 5.8 | 2.0 | 0.280 | 0.021 |
| 14 | 5.8 | 2.0 | 0.377 | 0.021 |
| 16 | 5.8 | 2.0 | 0.430 | 0.014 |
| 19 | 5.8 | 2.0 | 0.551 | 0.012 |
| 21 | 5.8 | 2.0 | 0.672 | 0.010 |
| 24 | 5.8 | 2.0 | 0.711 | 0.010 |
| 26 | 5.8 | 2.0 | 0.716 | 0.014 |

The results in the table show the inhibition of the acidification of water in contact with elemental sulfur as a result of the presence of NaCl in an environment populated by an abundant cellular biomass of *Thiobacilli* specifically introduced into the system.

Example 4

Inhibition Effect of NaCl on the Acidification of Water in Contact with Sulfur Powder To imitate the bacterial growth conditions in a natural environment, the same experiment as Example 1 was repeated without the inoculation of *Thiobacilli*.

The TM saline medium was compared with a medium consisting of rainwater sterilized at a low temperature by filtration on a membrane of cellulose nitrate (porosity 0.2 microns).

The experiment is aimed at verifying the inhibiting action of NaCl on the acidification of water rich and poor in nutrients in contact with elemental sulfur due to strains of the *Thiobacilli* type present in a natural environment.

The pH variations registered in the water are indicated in Table 2:

TABLE 2

| Time (days) | TM Medium | TM Medium + NaCl | Rainwater | Rainwater + NaCl |
|---|---|---|---|---|
| 0 | 6.0 | 6.0 | 6.0 | 6.0 |
| 2 | 6.0 | 6.0 | 6.0 | 6.0 |
| 4 | 6.0 | 6.0 | 6.0 | 6.0 |
| 7 | 4.0 | 6.0 | 5.0 | 6.0 |
| 9 | 3.0 | 6.0 | 3.5 | 6.0 |
| 11 | 2.5 | 6.0 | 3.0 | 6.0 |
| 14 | 2.5 | 6.0 | 2.5 | 6.0 |
| 21 | 1.8 | 5.8 | 1.8 | 5.8 |
| 23 | 1.8 | 5.8 | 1.8 | 5.8 |

The data of Table 2 show that the acidification of water in contact with elemental sulfur takes place in short periods of time also in systems which are not artificially inoculated and are exposed to the environment.

Acidification was also observed in the system poor in nutrients. In both cases the results confirm the inhibition effect on the part of NaCl.

Example 5

Inhibition Effect of NaCl on the Acidification of Water in Contact with Solid Sulfur The following experimental systems were prepared, using test samples of solid sulfur (discoid tables each of about 13 g).

System A: Containing 2 test samples not colonized by microbial cells, placed on the bottom of the container, completely immersed in rainwater (sterilized at a low temperature by micro-filtration);

System A1: Containing two non-colonized test samples, only dampened—by means of a sprayer—with rainwater sterilized by micro-filtration.

System B: Containing 2 colonized test samples (previously immersed in a suspension of $10^8$ cells/ml of *Thiobacilli* and left to dry in the air), placed on the bottom of the container, entirely immersed in micro-filtered rainwater;

System B1: Containing two colonized test samples as per the previous system, only dampened with rainwater sterilized by micro-filtration;

System C: Containing 2 colonized test samples entirely immersed in micro-filtered rainwater, in which 33 g/l of Nacl are dissolved;

System C1: containing 2 colonized test samples only dampened with rainwater sterilized by micro-filtration and containing 33 g/l of NaCl.

The pH variation measurements during 48 days of experimentation are represented in Table 4.

TABLE 4

| Time (days) | A | A1 | B | B1 | C | C1 |
|---|---|---|---|---|---|---|
| 0 | 6.0 | 6.0 | 6.0 | 6.0 | 6.0 | 6.0 |
| 3 | 6.0 | 3.5 | 3.5 | 3.5 | 6.0 | 5.8 |
| 5 | 6.0 | 3.5 | 3.5 | 2.5 | 6.0 | 5.8 |
| 7 | 6.0 | 3.5 | 3.5 | 2.5 | 5.8 | 5.8 |
| 10 | 6.0 | 3.0 | 3.0 | 2.5 | 5.8 | 5.8 |
| 12 | 6.0 | 3.0 | 3.0 | 2.5 | 5.8 | 5.8 |
| 15 | 5.8 | 3.0 | 3.0 | 2.5 | 5.8 | 5.8 |
| 21 | 5.8 | 3.0 | 2.5 | 2.5 | 5.8 | 5.8 |
| 29 | 5.8 | 2.5 | 2.5 | 2.5 | 5.8 | 5.8 |
| 32 | 5.8 | 2.5 | 2.5 | 2.0 | 5.8 | 5.8 |
| 35 | 5.8 | 2.5 | 2.0 | 2.0 | 5.8 | 5.8 |
| 38 | 5.8 | 2.0 | 1.8 | 1.8 | 5.8 | 5.8 |
| 42 | 5.8 | 2.0 | 1.6 | 1.6 | 5.8 | 5.8 |
| 46 | 5.8 | 2.0 | 1.5 | 1.5 | 5.8 | 5.8 |
| 48 | 5.8 | 2.0 | 1.3 | 1.3 | 5.8 | 5.8 |

The data indicated in Table 4 show the inhibition effect of the acidification of water in contact with surfaces of solid sulfur due to the presence of NaCl. The effect is evident in both the systems completely immersed in water and also in those only dampened on the surface.

Example 6

Comparison of the Inhibition of the Acidification of Water in Contact with Elemental Sulfur Between NaCl and the Bactericide Sodium-Lauryl-Sulfate (SLS)

The experiment was aimed at comparing the action of SLS, a known bacteriostatic for *Thiobacilli*, and Sodium Chloride on the same microbial consortium.

A series of 6 100 ml flasks containing 50 ml of TM medium (with 0.4 g of sulfur flowers), were inoculated with 1 ml of mixed culture containing $10^8$ cells/ml.

The tests comprised:
A—2 control flasks containing TM and sulfur, without NaCl;
B—2 flasks with TM, sulfur and 33 g/l of NaCl;
C—2 flasks with TM, sulfur and 20 mg/l of SLS (concentration used in literature as bacteriostatic)

The pH values and the bacterial growth were measured over a period of 34 days, by means of the increase in the absorbance. The results are indicated in Table 5.

TABLE 5

| Time (days) | O.D. | | | p.H. | | |
|---|---|---|---|---|---|---|
| | A | B | C | A | B | C |
| 0 | 0.014 | 0.014 | 0.014 | 6.0 | 6.0 | 6.0 |
| 3 | 0.028 | 0.015 | 0.013 | 3.5 | 6.0 | 4.5 |
| 5 | 0.069 | 0.017 | 0.042 | 2.5 | 6.0 | 4.5 |
| 8 | 0.176 | 0.023 | 0.073 | 2.0 | 5.8 | 4.0 |
| 11 | 0.320 | 0.028 | 0.067 | 2.0 | 5.8 | 4.0 |
| 16 | 0.512 | 0.025 | 0.098 | 1.8 | 5.8 | 3.8 |
| 21 | 0.593 | 0.026 | 0.080 | 1.8 | 5.8 | 3.8 |
| 23 | 0.613 | 0.022 | 0.035 | 1.5 | 5.8 | 3.8 |
| 28 | 0.631 | 0.022 | 0.033 | 1.5 | 5.8 | 3.2 |
| 31 | 0.652 | 0.026 | 0.020 | 1.5 | 5.8 | 3.2 |

The data in Table 5 show that both substances are capable of inhibiting the acidification of water in contact with elemental sulfur. The greater efficacy of the treatment with NaCl with respect to that with SLS is possibly due to the different concentrations used.

Example 7

Inhibition Effect of Different Salts on the Acidification of Water in Contact with Solid Sulfur The verification is aimed at discovering the effects deriving from the presence of different salts at varying concentrations on the same consortium.

A series of 12 100 ml flasks containing 50 ml of TM medium (with 0.4 g of sulfur powder), was inoculated with 1 ml of mixed culture containing $10^8$ cells/ml.

The test comprised:
3 control flasks containing TM and sulfur, with NaCl (0.16 M, 0.33 M, 0.56 M);
3 flasks with TM, sulfur and $Na_2SO_4$ (0.12 M, 0.24 M, 0.56 M);
3 flasks with TM, sulfur and KCl (0.13 M, 0.26 M, 0.56 M);
3 flasks with TM, sulfur and $KNO_3$ (0.09 M, 0.19 M, 0.56 M)

The data collected are listed in Table 6.

TABLE 6

| Time | NaCl(M) | | | $Na_2SO_4$(M) | | | KCl(M) | | | $KNO_3$(M) | | |
|---|---|---|---|---|---|---|---|---|---|---|---|---|
| Days | 0.16 | 0.33 | 0.56 | 0.12 | 0.24 | 0.56 | 0.13 | 0.26 | 0.56 | 0.09 | 0.19 | 0.5 |
| 0 | 6.0 | 6.0 | 6.0 | 6.0 | 6.0 | 6.0 | 6.0 | 6.0 | 6.0 | 6.0 | 6.0 | 6.0 |
| 2 | 6.0 | 6.0 | 6.0 | 6.0 | 6.0 | 6.0 | 6.0 | 6.0 | 6.0 | 6.0 | 6.0 | 6.0 |
| 6 | 3.5 | 5.5 | 6.0 | 3.5 | 4.5 | 6.0 | 4.5 | 5.5 | 6.0 | 3.8 | 4.8 | 6.0 |
| 9 | 2.8 | 5.0 | 6.0 | 2.8 | 4.0 | 6.0 | 4.0 | 5.5 | 6.0 | 3.0 | 4.0 | 6.0 |
| 12 | 2.8 | 3.0 | 6.0 | 2.8 | 3.5 | 6.0 | 3.5 | 5.5 | 6.0 | 3.0 | 4.0 | 6.0 |
| 15 | 2.5 | 3.0 | 6.0 | 2.8 | 3.0 | 5.9 | 3.0 | 5.5 | 6.0 | 3.0 | 4.0 | 6.0 |
| 18 | 2.5 | 3.0 | 6.0 | 2.5 | 2.8 | 5.9 | 3.0 | 5.2 | 6.0 | 3.0 | 4.0 | 6.0 |
| 20 | 2.5 | 2.5 | 6.0 | 1.8 | 2.0 | 5.9 | 3.0 | 5.2 | 6.0 | 3.0 | 4.0 | 6.0 |
| 24 | 2.0 | 2.5 | 6.0 | 1.8 | 2.0 | 5.9 | 2.5 | 5.0 | 6.0 | 3.0 | 4.0 | 6.0 |
| 28 | 1.7 | 1.9 | 6.0 | 1.6 | 1.7 | 5.9 | 2.5 | 5.0 | 6.0 | 3.0 | 4.0 | 6.0 |
| 30 | 1.6 | 1.7 | 6.0 | 1.6 | 1.5 | 5.9 | 2.4 | 5.0 | 6.0 | 3.0 | 3.3 | 6.0 |
| 40 | 1.3 | 1.4 | 5.8 | 1.4 | 1.5 | 5.8 | 1.5 | 4.9 | 5.8 | 3.0 | 3.2 | 5.8 |

The experiment indicates that the inhibiting action of the acidification of water in contact with elemental sulfur can not only be induced with NaCl but also with other salts such as nitrates and sulfates, at suitable concentrations.

Example 8

Inhibition of the Acidification of Water in Contact with Submersed Sulfur

Two blocks of elemental sulfur with an upper surface of approximately 2500 $cm^2$ (8.5 Kg of sulfur) are positioned in two containers. The upper surface of each block of sulfur is wetted with 250 ml of a bacterial suspension of *Thiobacilli* containing over $10^8$ bacteria per milliliter. The two blocks are subsequently submersed with rainwater. Sodium chloride is added to one of the containers until a concentration of 30 g/l is reached.

The containers are exposed to the outside environment for three months, care being taken to regularly replace the water possibly lost by evaporation. At the end of this period, the pH of the solution in the two containers is measured.

The following table shows the pH values registered in the two types of treatment. The efficacy of the treatment with inorganic salt in inhibiting the acidification of water in contact with sulfur, is evident. The pH variations registered in the water are indicated in Table 7.

TABLE 7

| Time | pH | |
|---|---|---|
| (days) | −NaCl | +NaCl |
| 0 | 6.0 | 6.0 |
| 10 | 3.0 | 5.9 |

TABLE 7-continued

| Time | pH | |
|---|---|---|
| (days) | −NaCl | +NaCl |
| 20 | 1.8 | 5.8 |
| 30 | 1.8 | 5.8 |
| 40 | 1.8 | 5.8 |
| 90 | 1.8 | 5.8 |

Example 9

Inhibition of the Acidification of Water in Contact with a Sulfur Surface Treated with Inorganic Salts and Protected with a Layer of Sand Two blocks of elemental sulfur with an upper surface of approximately 2500 $cm^2$ (8.5 Kg of sulfur) are positioned in two containers. The upper surface of each block of sulfur is wetted with 250 ml of a bacterial suspension of *Thiobacilli* containing over $10^8$ bacteria per milliliter. The surface of one block is then treated with sodium chloride by spreading about 150 g of salt in powder form uniformly distributed. The two blocks are subsequently covered with a 2 cm layer of sand and wetted at regular intervals of time with rainwater until the layer of sand is saturated and the rilling of excess water is produced with respect to the saturation. Rainwater is added every month in a quantity equivalent to a fall of 100 mm.

The containers are exposed to the outside environment for three months. At the end of this period, the pH of the water in contact with the sulfur in the two containers, is measured.

Table 8 shows the pH values registered in the two types of treatment. The efficacy of the treatment with inorganic salt in inhibiting the acidification of water in contact with sulfur, is evident.

TABLE 8

| Time | pH | |
|---|---|---|
| (days) | −NaCl | +NaCl |
| 0 | 6.0 | 6.0 |
| 10 | 3.0 | 5.8 |
| 20 | 1.8 | 5.7 |
| 30 | 1.8 | 5.7 |

TABLE 8-continued

| Time | pH | |
|---|---|---|
| (days) | −NaCl | +NaCl |
| 40 | 1.8 | 5.7 |
| 90 | 1.8 | 5.7 |

Example 10

Inhibition of the Acidification of Water in Contact with a Sulfur Surface Treated with Inorganic Salts Englobed in the Surface Layer of Sulfur Two blocks of elemental sulfur with an upper surface of approximately 2500 cm$^2$ (8.5 Kg of sulfur) are positioned in two containers. The surface of one block is then covered with a fine layer (3 mm) of liquid sulfur containing sodium chloride (10%). The upper surface of each block of sulfur is wetted with 250 ml of a bacterial suspension of *Thiobacilli* containing over 10$^8$ bacteria per milliliter. The two blocks are subsequently covered with a 2 cm layer of sand and wetted at regular intervals of time with rainwater until the layer of sand is saturated and the rilling of excess water is produced with respect to the saturation. Rainwater is added every month in a quantity equivalent to a fall of 100 mm.

The containers are exposed to the outside environment for three months. At the end of this period, the pH of the water in contact with the sulfur in the two containers, is measured.

Table 9 shows the pH values registered in the two types of treatment. The efficacy of the treatment with inorganic salt in inhibiting the acidification of water in contact with sulfur, is evident.

TABLE 9

| Time | pH | |
|---|---|---|
| (days) | −NaCl | +NaCl |
| 0 | 6.4 | 6.5 |
| 10 | 3.0 | 6.5 |
| 20 | 1.8 | 6.5 |
| 30 | 1.8 | 6.5 |
| 90 | 1.8 | 6.5 |

The invention claimed is:

1. A method for inhibiting biological acidification of water that contacts materials containing sulfur in reduced form or elemental sulfur, the materials being susceptible to oxidation by *Thiobacilli*, the method comprising:
   bringing the materials into contact with a soluble inorganic salt;
   wherein:
   the soluble inorganic salt comprises chlorides, sulfates or nitrates of mono- or bivalent cations;
   the soluble inorganic salt is applied in an amount sufficient to provide a concentration of the soluble inorganic salt in the water of from 0.4 normal to saturation;
   bringing the materials into contact with a soluble inorganic salt comprises spreading the soluble inorganic salt over the materials, and subsequently spreading a cover over the materials; and
   the cover consists of granulated materials optionally containing small quantities of hydraulic binders.

2. The method according to claim 1, wherein:
   the soluble inorganic salt comprises NaCl; and
   the soluble inorganic salt is applied in an amount sufficient to maintain a concentration of the soluble inorganic salt in the water of from 0.5 N to saturation.

3. The method according to claim 1, wherein:
   the granulated materials are selected from the group consisting of sand, breccia, pozzolan, soil, and excavation materials; and
   the binders are selected from the group consisting of lime and cement.

4. The method according to claim 1, wherein the initial concentration of salt is maintained by additions of concentrated saline solutions.

5. The method according to claim 1, wherein the materials are placed below groundwater level.

6. The method according to claim 1, wherein the materials are contained by a containment wall having a height less than or equal to the thickness of the cover.

7. A method for inhibiting biological acidification of water that contacts materials containing sulfur in reduced form or elemental sulfur, the materials being susceptible to oxidation by *Thiobacilli*, the method comprising:
   bringing the materials into contact with a soluble inorganic salt;
   wherein:
   the soluble inorganic salt comprises chlorides, sulfates or nitrates of mono- or bivalent cations;
   the soluble inorganic salt is applied in an amount sufficient to provide a concentration of the soluble inorganic salt in the water of from 0.4 normal to saturation;
   bringing the materials into contact with a soluble inorganic salt comprises spreading a suspension of the inorganic salt in liquid sulfur over the materials; and
   the inorganic salt is present in the suspension at a concentration of from 5 to 20% by weight.

8. The method according to claim 7, wherein the materials are placed below groundwater level.

* * * * *